US012629200B2

(12) United States Patent
Malang et al.

(10) Patent No.: US 12,629,200 B2
(45) Date of Patent: May 19, 2026

(54) SURGICAL INSTRUMENTS, SYSTEMS, AND METHODS INCORPORATING ULTRASONIC AND ELECTROSURGICAL FUNCTIONALITY

(71) Applicant: Covidien LP, Mansfield, MA (US)

(72) Inventors: Keith W. Malang, Longmont, CO (US); Richard L. Croft, Mead, CO (US); Kenneth E. Netzel, Loveland, CO (US); Matthew S. Cowley, Frederick, CO (US); James R. Fagan, Erie, CO (US); Michael B. Lyons, Boulder, CO (US); David J. Van Tol, Boulder, CO (US)

(73) Assignee: Covidien LP, Mansfield, MA (US)

( * ) Notice: Subject to any disclaimer, the term of this patent is extended or adjusted under 35 U.S.C. 154(b) by 270 days.

(21) Appl. No.: 18/558,683

(22) PCT Filed: Apr. 25, 2022

(86) PCT No.: PCT/IB2022/053820
§ 371 (c)(1),
(2) Date: Nov. 2, 2023

(87) PCT Pub. No.: WO2022/234389
PCT Pub. Date: Nov. 10, 2022

(65) Prior Publication Data
US 2024/0238039 A1 Jul. 18, 2024

Related U.S. Application Data

(60) Provisional application No. 63/183,330, filed on May 3, 2021.

(51) Int. Cl.
A61B 17/32 (2006.01)
A61B 18/14 (2006.01)
(Continued)

(52) U.S. Cl.
CPC ..................... *A61B 18/1447* (2013.01); *A61B 2017/00106* (2013.01); *A61B 2017/320074* (2017.08);
(Continued)

(58) Field of Classification Search
CPC ....... A61B 2017/320074; A61B 2017/320095; A61B 2018/00875; A61B 2018/00898; A61B 2018/00994
See application file for complete search history.

(56) References Cited

U.S. PATENT DOCUMENTS 5,190,517 A 3/1993 Zieve et al.
5,312,329 A 5/1994 Beaty et al.
(Continued)

FOREIGN PATENT DOCUMENTS

WO 2017003850 A1 1/2017

OTHER PUBLICATIONS

International Search Report and Written Opinion issued in corresponding International Application No. PCT/ IB2022/053820 mailed Jul. 29, 2022, 15 pages.
(Continued)

*Primary Examiner* — Daniel W Fowler

(57) ABSTRACT

A surgical system includes an ultrasonic blade operably coupled to an ultrasonic transducer, a jaw member pivotable relative to the blade for clamping tissue between the blade and the jaw member, and at least one controller. A portion of the jaw member is adapted to connect to a source of electrosurgical energy at a first potential and another portion of the jaw member or the blade is adapted to connect to the source of electrosurgical energy at a second potential to conduct electrosurgical energy therebetween and through the clamped tissue. The blade is configured to transmit ultrasonic energy to the tissue clamped between the blade and the jaw member. The at least one controller is configured
(Continued)

to monitor a resonant frequency associated with the ultrasonic energy and to monitor an impedance of the clamped tissue associated with the electrosurgical energy and to determine whether an adverse condition exists based thereon.

20 Claims, 8 Drawing Sheets

(51) Int. Cl.
    *A61B 17/00*         (2006.01)
    *A61B 18/00*         (2006.01)

(52) U.S. Cl.
    CPC ............. *A61B 2017/320095* (2017.08); *A61B 2018/0063* (2013.01); *A61B 2018/00845* (2013.01); *A61B 2018/00875* (2013.01); *A61B 2018/00898* (2013.01); *A61B 2018/00904* (2013.01); *A61B 2018/00994* (2013.01)

(56) References Cited

U.S. PATENT DOCUMENTS

| | | | |
|---|---|---|---|
| 5,443,463 | A | 8/1995 | Stern et al. |
| 6,251,110 | B1 | 6/2001 | Wampler |
| 6,257,241 | B1 | 7/2001 | Wampler |
| 6,416,486 | B1 | 7/2002 | Wampler |
| 6,562,032 | B1 | 5/2003 | Ellman et al. |
| 6,648,839 | B2 | 11/2003 | Manna et al. |
| 6,736,814 | B2 | 5/2004 | Manna et al. |
| 6,902,536 | B2 | 6/2005 | Manna et al. |
| 7,717,913 | B2 | 5/2010 | Novak et al. |
| 7,717,915 | B2 | 5/2010 | Miyazawa |
| 7,905,881 | B2 | 3/2011 | Masuda et al. |
| 7,909,824 | B2 | 3/2011 | Masuda et al. |
| 8,048,074 | B2 | 11/2011 | Masuda |
| 8,147,488 | B2 | 4/2012 | Masuda |
| 8,382,748 | B2 | 2/2013 | Geisel |
| 8,663,220 | B2 | 3/2014 | Wiener et al. |
| 8,663,223 | B2 | 3/2014 | Masuda et al. |
| 8,773,001 | B2 | 7/2014 | Wiener et al. |
| 9,039,690 | B2 | 5/2015 | Kersten et al. |
| 9,326,787 | B2 | 5/2016 | Sanai et al. |
| 9,364,279 | B2 | 6/2016 | Houser et al. |
| 9,592,072 | B2 | 3/2017 | Akagane |
| 9,681,912 | B2 | 6/2017 | Tsubuku et al. |
| 9,700,366 | B2 | 7/2017 | Paulus |
| 9,757,142 | B2 | 9/2017 | Shimizu |
| 9,764,164 | B2 | 9/2017 | Wiener et al. |
| 9,808,305 | B2 | 11/2017 | Hareyama et al. |
| 9,901,754 | B2 | 2/2018 | Yamada |
| 9,949,785 | B2 | 4/2018 | Price et al. |
| 10,010,339 | B2 | 7/2018 | Witt et al. |
| 10,045,794 | B2 | 8/2018 | Witt et al. |
| 10,045,815 | B2 | 8/2018 | Tsubuku |
| 10,172,671 | B2 | 1/2019 | Masuda et al. |
| 10,245,065 | B2 | 4/2019 | Witt et al. |
| 10,265,094 | B2 | 4/2019 | Witt et al. |
| 10,357,273 | B2 | 7/2019 | Akagane |
| 10,433,865 | B2 | 10/2019 | Witt et al. |
| 10,433,866 | B2 | 10/2019 | Witt et al. |
| 10,433,896 | B2 | 10/2019 | Assmus et al. |
| 10,463,887 | B2 | 11/2019 | Witt et al. |
| 10,470,791 | B2 | 11/2019 | Houser |
| 10,575,895 | B2 | 3/2020 | Shelton, IV et al. |
| 10,610,286 | B2 | 4/2020 | Wiener et al. |
| 10,624,692 | B2 | 4/2020 | Akagane et al. |
| 10,631,861 | B2 | 4/2020 | Shelton, IV et al. |
| 10,660,692 | B2 | 5/2020 | Lesko et al. |
| 10,687,884 | B2 | 6/2020 | Wiener et al. |
| 10,688,321 | B2 | 6/2020 | Wiener et al. |
| 10,716,615 | B2 | 7/2020 | Shelton, IV et al. |
| 10,765,470 | B2 | 9/2020 | Yates et al. |
| 10,842,523 | B2 | 11/2020 | Shelton, IV et al. |
| 10,856,927 | B2 | 12/2020 | Lau et al. |
| 10,888,347 | B2 | 1/2021 | Witt et al. |
| 10,898,256 | B2 | 1/2021 | Yates et al. |
| 10,932,808 | B2 | 3/2021 | Shelton, IV et al. |
| 10,945,778 | B2 | 3/2021 | Weisenburgh, II et al. |
| 10,945,779 | B2 | 3/2021 | Weisenburgh, II et al. |
| 10,966,745 | B2 | 4/2021 | Akagane |
| 10,973,541 | B2 | 4/2021 | Madan et al. |
| 2007/0173872 | A1 | 7/2007 | Neuenfeldt |
| 2008/0294156 | A1* | 11/2008 | Newton ............ A61B 18/1206 |
| | | | 606/34 |
| 2010/0145335 | A1 | 6/2010 | Johnson et al. |
| 2011/0082486 | A1 | 4/2011 | Messerly et al. |
| 2012/0150176 | A1 | 6/2012 | Weizman |
| 2014/0135804 | A1 | 5/2014 | Weisenburgh, II et al. |
| 2014/0330271 | A1 | 11/2014 | Dietz et al. |
| 2015/0148804 | A1 | 5/2015 | Rooks et al. |
| 2015/0164533 | A1 | 6/2015 | Felder et al. |
| 2015/0182251 | A1 | 7/2015 | Messerly et al. |
| 2016/0038220 | A1 | 2/2016 | Twomey |
| 2017/0007317 | A1 | 1/2017 | Allen, IV et al. |
| 2017/0105754 | A1 | 4/2017 | Boudreaux et al. |
| 2017/0164973 | A1 | 6/2017 | Lesko et al. |
| 2017/0202605 | A1 | 7/2017 | Shelton, IV et al. |
| 2017/0202609 | A1 | 7/2017 | Shelton, IV et al. |
| 2017/0238991 | A1 | 8/2017 | Worrell et al. |
| 2017/0340345 | A1* | 11/2017 | Yates ................ A61B 17/3211 |
| 2019/0216492 | A1 | 7/2019 | Meiser et al. |
| 2019/0274717 | A1* | 9/2019 | Nott .............. A61B 17/320092 |
| 2020/0078089 | A1 | 3/2020 | Henderson et al. |
| 2021/0038292 | A1 | 2/2021 | Kabala et al. |

OTHER PUBLICATIONS

International Preliminary Report on Patentability and Written Opinion issued in corresponding International Application No. PCT/IB2022/053820 dated Oct. 24, 2023, 10 pages.

* cited by examiner

SURGICAL INSTRUMENTS, SYSTEMS, AND METHODS INCORPORATING ULTRASONIC AND ELECTROSURGICAL FUNCTIONALITY

CROSS-REFERENCE TO RELATED APPLICATION

This application is a 371 National Stage Application of International Application No. PCT/IB2022/053820, filed Apr. 25, 2022, which claims the benefit of, and priority to, U.S. Provisional Patent Application No. 63/183,330, filed on May 3, 2021, the entire contents of each of which are hereby incorporated herein by reference.

FIELD

The present disclosure relates to energy-based surgical instruments and, more particularly, to surgical instruments, systems, and methods incorporating ultrasonic and electrosurgical functionality to facilitate energy-based tissue treatment.

BACKGROUND

Ultrasonic surgical instruments and systems utilize ultrasonic energy, i.e., ultrasonic vibrations, to treat tissue. More specifically, ultrasonic surgical instruments and systems utilize mechanical vibration energy transmitted at ultrasonic frequencies to treat tissue. An ultrasonic surgical device may include, for example, an ultrasonic blade and a clamp mechanism to enable clamping of tissue against the blade. Ultrasonic energy transmitted to the blade causes the blade to vibrate at very high frequencies, which allows for heating tissue to treat tissue clamped against or otherwise in contact with the blade.

Electrosurgical instruments and systems conduct Radio Frequency (RF) energy through tissue to treat tissue. An electrosurgical instrument or system may be configured to conduct bipolar RF energy between oppositely charged electrodes and through tissue, e.g., tissue clamped between the electrodes or otherwise in contact therewith, to treat tissue. Alternatively or additionally, an electrosurgical instrument or system may be configured to deliver monopolar RF energy from an active electrode to tissue in contact with the electrode, with the energy returning via a remote return electrode device to complete the circuit.

SUMMARY

As used herein, the term "distal" refers to the portion that is described which is further from an operator (whether a human surgeon or a surgical robot), while the term "proximal" refers to the portion that is being described which is closer to the operator. Terms including "generally," "about," "substantially," and the like, as utilized herein, are meant to encompass variations, e.g., manufacturing tolerances, material tolerances, use and environmental tolerances, measurement variations, and/or other variations, up to and including plus or minus 10 percent. Further, any or all of the aspects described herein, to the extent consistent, may be used in conjunction with any or all of the other aspects described herein.

Provided in accordance with aspects of the present disclosure is a surgical system including an ultrasonic blade operably coupled to an ultrasonic transducer for receiving ultrasonic energy produced by the ultrasonic transducer, a jaw member pivotable relative to the ultrasonic blade between a spaced-apart position and an approximated position for clamping tissue between the ultrasonic blade and the jaw member, and at least one controller. A portion of the jaw member is adapted to connect to a source of electrosurgical energy at a first potential and another portion of the jaw member or the ultrasonic blade is adapted to connect to the source of electrosurgical energy at a second potential different from the first potential to conduct electrosurgical energy therebetween and through the clamped tissue. The ultrasonic blade is configured to transmit ultrasonic energy to the tissue clamped between the ultrasonic blade and the jaw member. The at least one controller is configured to monitor a resonant frequency associated with the ultrasonic energy and to monitor an impedance of the clamped tissue associated with the electrosurgical energy and to determine whether an adverse condition exists based thereon.

In an aspect of the present disclosure, the controller is configured to determine that an adverse condition exists when it is determined that an expected change in impedance did not occur and that an expected decrease in resonant frequency did not occur. In such or other aspects, the adverse condition is a wet field condition.

In another aspect of the present disclosure, the controller is further configured, in response to determining that the adverse condition exists, to provide an indication that the adverse condition exists.

In still another aspect of the present disclosure, the controller is further configured, in response to determining that the adverse condition exists, to modify at least one of the ultrasonic energy or the electrosurgical energy. Modifying the energy may include turning off at least one of the ultrasonic energy or the electrosurgical energy.

In yet another aspect of the present disclosure, the electrosurgical energy is configured to facilitate tissue treatment in conjunction with the ultrasonic energy. Alternatively, the ultrasonic energy is configured to treat tissue and the electrosurgical energy is configured to interrogate tissue.

In still yet another aspect of the present disclosure, monitoring the resonant frequency includes monitoring at least one of: a value of the resonant frequency, a ramp (e.g., rate of change) of the resonant frequency, or a change in the resonant frequency. Additionally or alternatively, monitoring the impedance of the clamped tissue includes monitoring at least one of: a value of the impedance, a ramp of the impedance, or a change in the impedance.

A method of energy-based tissue treatment provided in accordance with aspects of the present disclosure includes transmitting ultrasonic energy, via an ultrasonic blade, to tissue clamped between the ultrasonic blade and a jaw member; energizing a portion of the jaw member with electrosurgical energy at a first potential and energizing another portion of the jaw member or the ultrasonic blade with electrosurgical energy at a second potential different from the first potential to conduct electrosurgical energy therebetween and through the clamped tissue; monitoring a resonant frequency associated with the ultrasonic energy; monitoring an impedance of the clamped tissue associated with the electrosurgical energy; and determining whether an adverse condition exists based on the monitoring of the resonant frequency and the monitoring of the impedance.

In an aspect of the present disclosure, it is determined that an adverse condition exists when it is determined that an expected change, e.g., rise, decrease, or other suitable pattern such as, for example, decrease followed by a rise, in impedance did not occur and that an expected decrease in resonant frequency did not occur. In these or other aspects, the adverse condition is a wet field condition.

In another aspect of the present disclosure, in response to determining that the adverse condition exists, an indication that the adverse condition exists is provided and/or at least one of the ultrasonic energy or the electrosurgical energy is modified, e.g., turned off.

In yet another aspect of the present disclosure, the electrosurgical energy is configured to facilitate tissue treatment in conjunction with the ultrasonic energy. Alternatively, the ultrasonic energy is configured to treat tissue and the electrosurgical energy is configured to interrogate tissue.

In still another aspect of the present disclosure, the monitoring of the resonant frequency includes monitoring at least one of: a value of the resonant frequency, a ramp of the resonant frequency, or a change in the resonant frequency. Additionally or alternatively, the monitoring of the impedance includes monitoring at least one of: a value of the impedance, a ramp of the impedance, or a change in the impedance.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1:
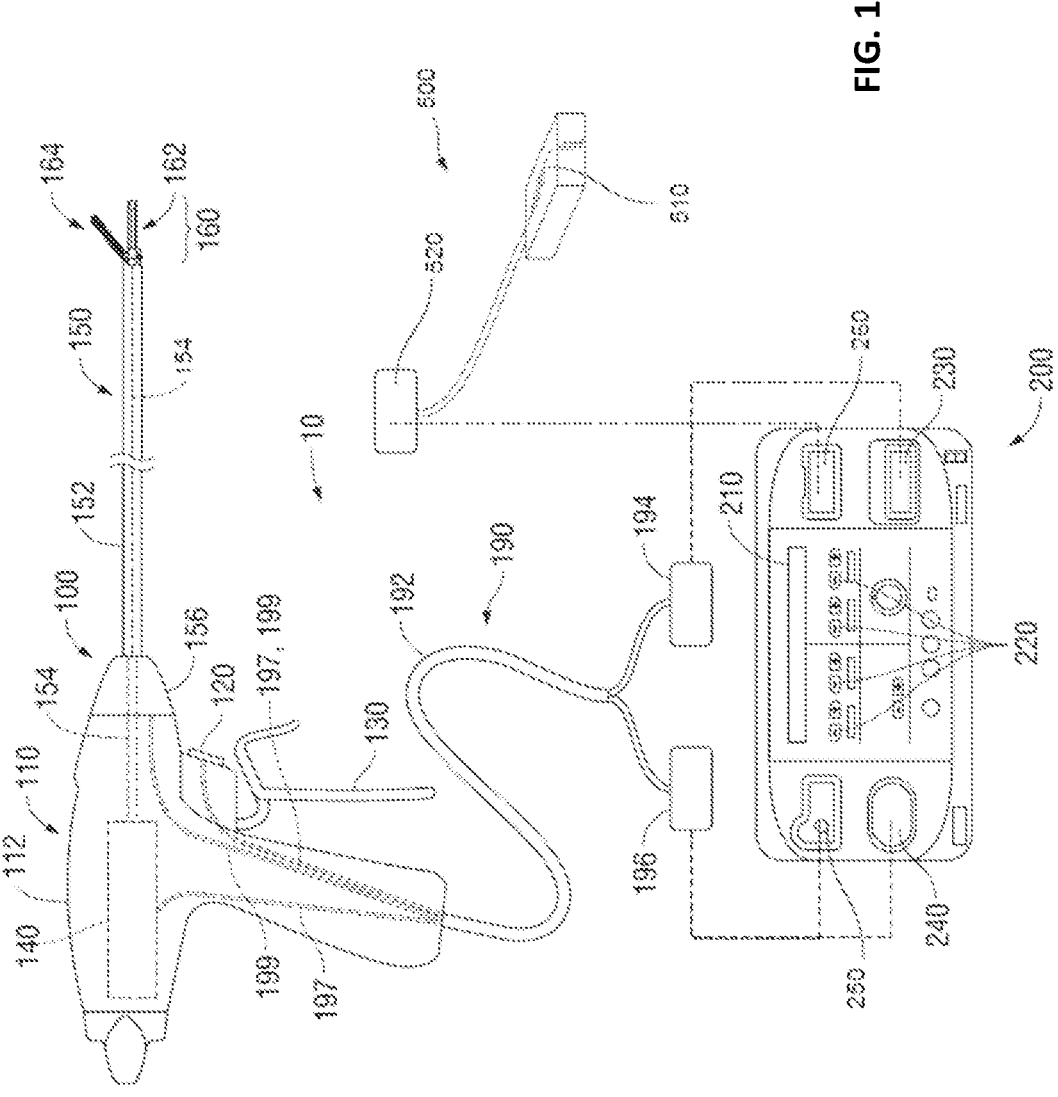
FIG. 1 is a side view of a surgical system provided in accordance with the present disclosure including a surgical instrument, a surgical generator, and a return electrode device.

Referring to FIG. 1, a surgical system provided in accordance with aspects of the present disclosure is shown generally identified by reference numeral 10 including a surgical instrument 100, a surgical generator 200, and, in some aspects, a return electrode device 500, e.g., including a return pad 510. Surgical instrument 100 includes a handle assembly 110, an elongated assembly 150 extending distally from handle assembly 110, an end effector assembly 160 disposed at a distal end of elongated assembly 150, and a cable assembly 190 operably coupled with handle assembly 110 and extending therefrom for connection to surgical generator 200.

Surgical generator 200 includes a display 210, a plurality user interface features 220, e.g., buttons, touch screens, switches, etc., an ultrasonic plug port 230, a bipolar electrosurgical plug port 240, and active and return monopolar electrosurgical plug ports 250, 260, respectively. As an alternative to plural dedicated ports 230-260, one or more common ports (not shown) may be configured to act as any two or more of ports 230-260.

Surgical instrument 100 is configured to operate in one or more electrosurgical modes supplying Radio Frequency (RF) energy to tissue to treat tissue, e.g., a monopolar configuration and/or a bipolar configuration, and an ultrasonic mode supplying ultrasonic energy to tissue to treat tissue. Surgical generator 200 is configured to produce ultrasonic drive signals for output through ultrasonic plug port 230 to surgical instrument 100 to activate surgical instrument 100 in the ultrasonic mode and to provide electrosurgical energy, e.g., RF bipolar energy for output through bipolar electrosurgical plug port 240 and/or RF monopolar energy for output through active monopolar electrosurgical port 250 to surgical instrument 100 to activate surgical instrument 100 in the one or more electrosurgical modes. Plug 520 of return electrode device 500 is configured to connect to return monopolar electrosurgical plug port 260 to return monopolar electrosurgical energy from surgical instrument 100 in the monopolar electrosurgical mode.

Continuing with reference to FIG. 1, handle assembly 110 includes a housing 112, an activation button 120, and a clamp trigger 130. Housing 112 is configured to support an ultrasonic transducer 140. Ultrasonic transducer 140 may be permanently engaged within housing 112 or removable therefrom. Ultrasonic transducer 140 includes a piezoelectric stack other suitable ultrasonic transducer components electrically coupled to surgical generator 200, e.g., via one or more of first electrical lead wires 197, to enable communication of ultrasonic drive signals to ultrasonic transducer 140 to drive ultrasonic transducer 140 to produce ultrasonic vibration energy that is transmitted along a waveguide 154 of elongated assembly 150 to blade 162 of end effector assembly 160 of elongated assembly 150, as detailed below. Feedback and/or control signals may likewise be communicated between ultrasonic transducer 140 and surgical generator 200. Ultrasonic transducer 140, more specifically, may include a stack of piezoelectric elements secured, under pre-compression between proximal and distal end masses or a proximal end mass and an ultrasonic horn with first and second electrodes electrically coupled between piezoelectric elements of the stack of piezoelectric elements to enable energization thereof to produce ultrasonic energy. However, other suitable ultrasonic transducer configurations, including plural transducers and/or non-longitudinal, e.g., torsional, transducers are also contemplated.

An activation button 120 is disposed on housing 112 and coupled to or between ultrasonic transducer 140 and/or surgical generator 200, e.g., via one or more of first electrical lead wires 197, to enable activation of ultrasonic transducer 140 in response to depression of activation button 120. In some configurations, activation button 120 may include an ON/OFF switch. In other configurations, activation button 120 may include multiple actuation switches to enable activation from an OFF position to different actuated positions corresponding to different activation settings, e.g., a first actuated position corresponding to a first activation setting (such as a LOW power or tissue sealing setting) and a second actuated position corresponding to a second activation setting (such as a HIGH power or tissue transection setting). In still other configurations, separate activation buttons may be provided, e.g., a first actuation button for activating a first activation setting and a second activation button for activating a second activation setting. Additional activation buttons, sliders, wheels, etc. are also contemplated to enable control of various different activation settings from housing 112.

Elongated assembly 150 of surgical instrument 100 includes an outer drive sleeve 152, an inner support sleeve 153 (FIG. 4) disposed within outer drive sleeve 152, a waveguide 154 extending through inner support sleeve 153 (FIG. 4), a drive assembly (not shown), a rotation knob 156, and an end effector assembly 160 including a blade 162 and a jaw member 164. Rotation knob 156 is rotatable in either direction to rotate elongated assembly 150 in either direction relative to handle assembly 110. The drive assembly operably couples a proximal portion of outer drive sleeve 152 to clamp trigger 130 of handle assembly 110. A distal portion of outer drive sleeve 152 is operably coupled to jaw member 164 and a distal end of inner support sleeve 153 (FIG. 4) pivotably supports jaw member 164. As such, clamp trigger 130 is selectively actuatable to thereby move outer drive sleeve 152 about inner support sleeve 153 (FIG. 4) to pivot jaw member 164 relative to blade 162 of end effector assembly 160 from a spaced apart position to an approximated position for clamping tissue between jaw member 164 and blade 162. The configuration of outer and inner sleeves 152, 153 (FIG. 4) may be reversed, e.g., wherein outer sleeve 152 is the support sleeve and inner sleeve 153 (FIG. 4) is the drive sleeve. Other suitable drive structures as opposed to a sleeve are also contemplated such as, for example, drive rods, drive cables, drive screws, etc.

Referring still to FIG. 1, the drive assembly may be tuned to provide a jaw clamping force, or jaw clamping force within a jaw clamping force range, to tissue clamped between jaw member 164 and blade 162 or may include a force limiting feature whereby the clamping force applied to tissue clamped between jaw member 164 and blade 162 is limited to a particular jaw clamping force or a jaw clamping force within a jaw clamping force range.

Figure 4:
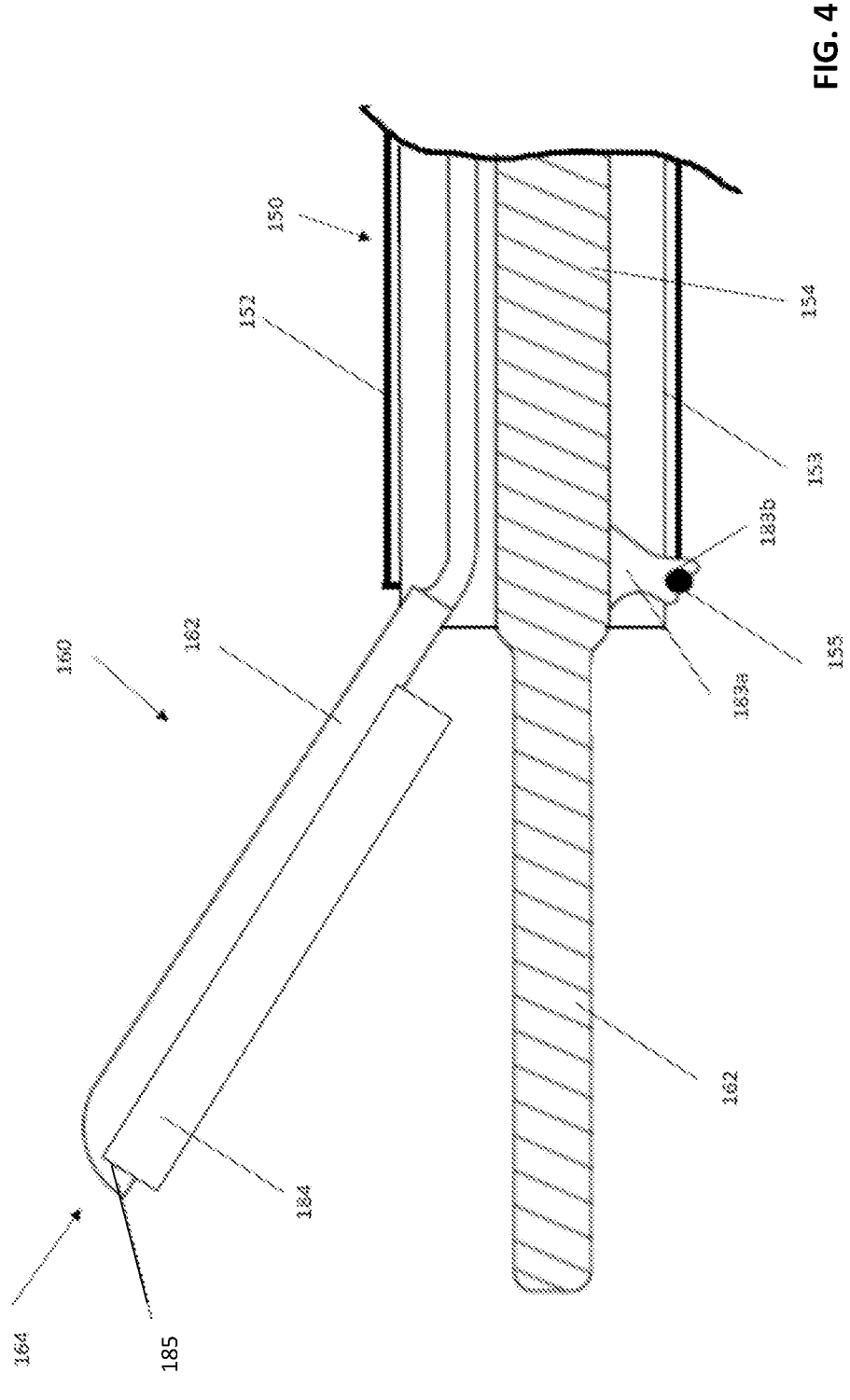
FIG. 4 is a longitudinal, cross-sectional view of a distal end portion of the surgical instrument of FIG. 1.

Waveguide 154, as noted above, extends from handle assembly 110 through inner sleeve 153 (FIG. 4). Waveguide 154 includes blade 162 disposed at a distal end thereof. Blade 162 may be integrally formed with waveguide 154, separately formed and subsequently attached (permanently or removably) to waveguide 154, or otherwise operably coupled with waveguide 154. Waveguide 154 and/or blade 162 may be formed from titanium, a titanium alloy, or other suitable electrically conductive material(s), although non-conductive materials are also contemplated. Waveguide 154 includes a proximal connector (not shown), e.g., a threaded male connector, configured for engagement, e.g., threaded engagement within a threaded female receiver, of ultrasonic transducer 140 such that ultrasonic motion produced by ultrasonic transducer 140 is transmitted along waveguide 154 to blade 162 for treating tissue clamped between blade 162 and jaw member 164 or positioned adjacent to blade 162.

Cable assembly 190 of surgical instrument 100 includes a cable 192, an ultrasonic plug 194, and an electrosurgical plug 196. Ultrasonic plug 194 is configured for connection with ultrasonic plug port 230 of surgical generator 200 while electrosurgical plug 196 is configured for connection with bipolar electrosurgical plug port 240 of surgical generator 200 and/or active monopolar electrosurgical plug port 250 of surgical generator 200. In configurations where generator 200 includes a common port, cable assembly 190 may include a common plug (not shown) configured to act as both the ultrasonic plug 194 and the electrosurgical plug 196. In configurations where surgical instrument 100 is only configured for ultrasonic operation, electrosurgical plug 196 and associated components are omitted.

Plural first electrical lead wires 197 electrically coupled to ultrasonic plug 194 extend through cable 192 and into handle assembly 110 for electrical connection to ultrasonic transducer 140 and/or activation button 120 to enable the selective supply of ultrasonic drive signals from surgical generator 200 to ultrasonic transducer 140 upon activation of activation button 120 in an ultrasonic mode. In addition, plural second electrical lead wires 199 are electrically coupled to electrosurgical plug 196 and extend through cable 192 into handle assembly 110. In bipolar configurations, separate second electrical lead wires 199 are electrically coupled to waveguide 154 and jaw member 164 (and/or different portions of jaw member 164) such that bipolar electrosurgical energy may be conducted between blade 162 and jaw member 164 (and/or between different portions of jaw member 164). In monopolar configurations, a second electrical lead wire 199 is electrically coupled to waveguide 154 such that monopolar electrosurgical energy may be supplied to tissue from blade 162. Alternatively or additionally, a second electrical lead wire 199 may electrically couple to jaw member 164 in the monopolar configuration to enable monopolar electrosurgical energy to be supplied to tissue from jaw member 164. In configurations where both bipolar and monopolar functionality are enabled, one or more of the second electrical lead wires 199 may be used for both the delivery of bipolar energy and monopolar energy; alternatively, bipolar and monopolar energy delivery may be provided by separate second electrical lead wires 199. One or more other second electrical lead wires 199 is electrically coupled to activation button 120 to enable the selective supply of electrosurgical energy from surgical generator 200 to waveguide 154 and/or jaw member 164 upon activation of activation button 120 in an electrosurgical mode(s).

Figure 2:
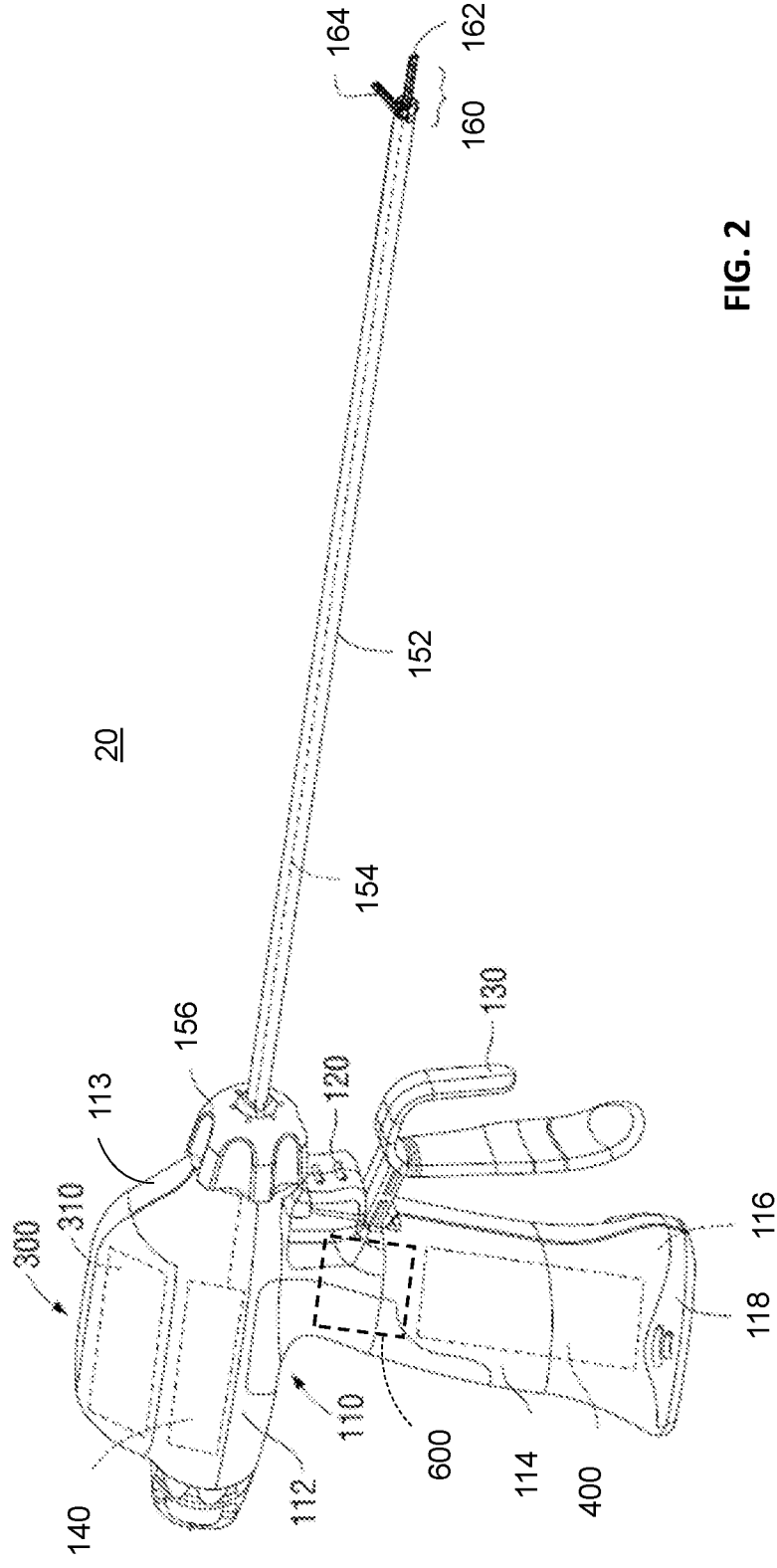
FIG. 2 is perspective view of another surgical system provided in accordance with the present disclosure including a surgical instrument incorporating an ultrasonic generator, electrosurgical generator, and power source therein.

As an alternative to a remote generator 200, surgical system 10 may be at least partially cordless in that it incorporates an ultrasonic generator, an electrosurgical generator, and/or a power source, e.g., a battery, thereon or therein. In this manner, the connections from surgical instrument 100 to external devices, e.g., generator(s) and/or power source(s), is reduced or eliminated. More specifically, with reference to FIG. 2, another surgical system in accordance with the present disclosure is shown illustrated as a surgical instrument 20 supporting an ultrasonic generator 310, a power source (e.g., battery assembly 400), and an electrosurgical generator 600 thereon or therein. Surgical instrument 20 is similar to surgical instrument 100 (FIG. 1) and may include any of the features thereof except as explicitly contradicted below. Accordingly, only differences between surgical instrument 20 and surgical instrument 100 (FIG. 1) are described in detail below while similarities are omitted or summarily described.

Housing 112 of surgical instrument 20 includes a body portion 113 and a fixed handle portion 114 depending from body portion 113. Body portion 113 of housing 112 is configured to support an ultrasonic transducer and generator assembly ("TAG") 300 including ultrasonic generator 310 and ultrasonic transducer 140. TAG 300 may be perma-
nently engaged with body portion 113 of housing 112 or
removable therefrom.

Fixed handle portion 114 of housing 112 defines a com-
partment 116 configured to receive battery assembly 400 and
electrosurgical generator 600 and a door 118 configured to
enclose compartment 116. An electrical connection assem-
bly (not shown) is disposed within housing 112 and serves
to electrically couple activation button 120, ultrasonic gen-
erator 310 of TAG 300, and battery assembly 400 with one
another when TAG 300 is supported on or in body portion
113 of housing 112 and battery assembly 400 is disposed
within compartment 116 of fixed handle portion 114 of
housing 112, thus enabling activation of surgical instrument
20 in an ultrasonic mode in response to appropriate actuation
of activation button 120. Further, the electrical connection
assembly or a different electrical connection assembly dis-
posed within housing 112 serves to electrically couple
activation button 120, electrosurgical generator 600, battery
assembly 400, and end effector assembly 160 (e.g., blade
162 and jaw member 164 and/or different portions of jaw
member 164) with one another when electrosurgical gen-
erator 600 and battery assembly 400 are disposed within
compartment 116 of fixed handle portion 114 of housing
112, thus enabling activation of surgical instrument 20 in an
electrosurgical mode, e.g., bipolar RF, in response to appro-
priate actuation of activation button 120. For a monopolar
electrosurgical mode, return electrode device 500 (FIG. 1)
may be configured to connect to surgical instrument 20
(electrosurgical generator 600 thereof, more specifically), to
complete a monopolar circuit through tissue and between
surgical instrument 20 (e.g., blade 162 and/or jaw member
164) and return electrode device 500 (FIG. 1).

Figure 3:
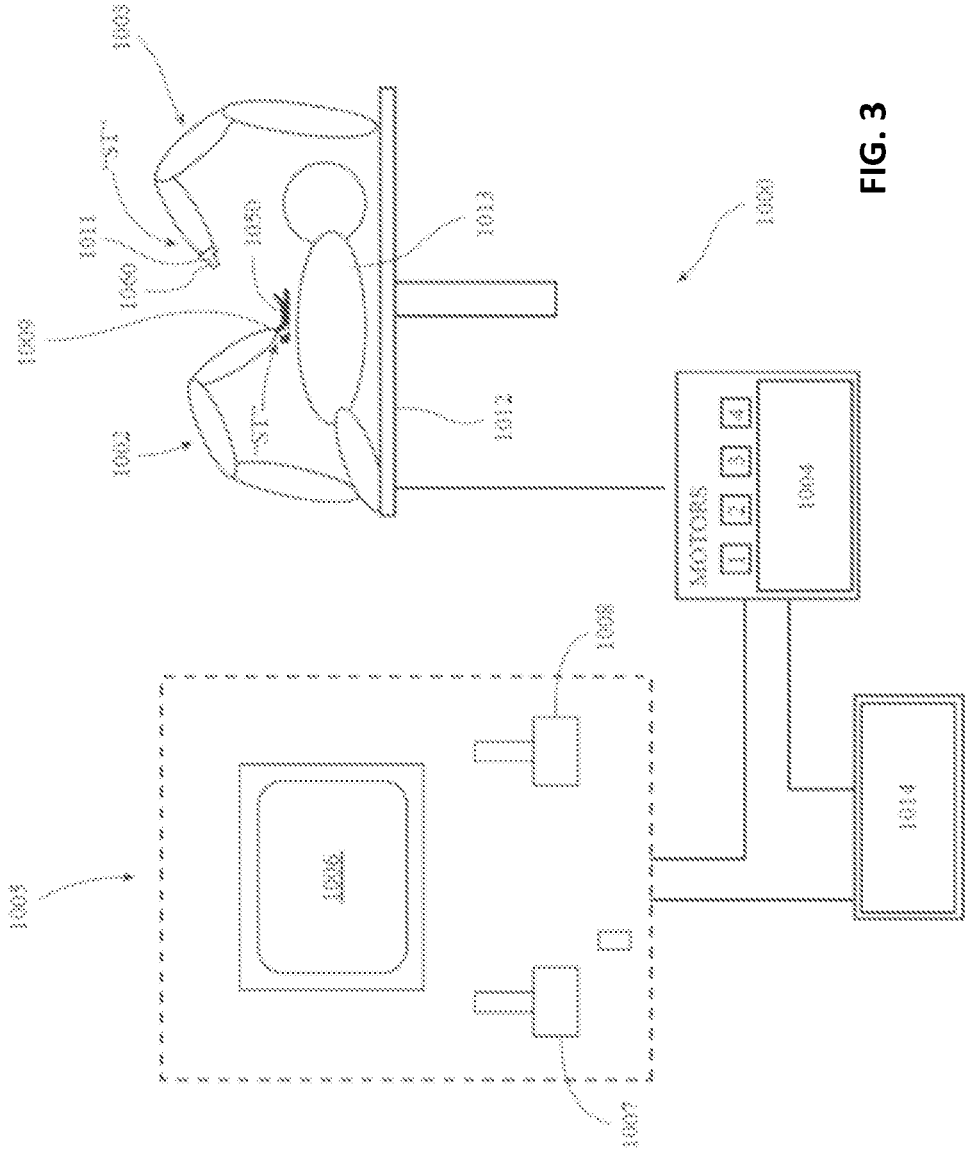
FIG. 3 is a schematic illustration of a robotic surgical system provided in accordance with the present disclosure.

Turning to FIG. 3, a robotic surgical system in accordance
with the aspects and features of the present disclosure is
shown generally identified by reference numeral 1000. For
the purposes herein, robotic surgical system 1000 is gener-
ally described. Aspects and features of robotic surgical
system 1000 not germane to the understanding of the present
disclosure are omitted to avoid obscuring the aspects and
features of the present disclosure in unnecessary detail.

Robotic surgical system 1000 generally includes a plu-
rality of robot arms 1002, 1003; a control device 1004; and
an operating console 1005 coupled with control device
1004. Operating console 1005 may include a display device
1006, which may be set up in particular to display three
dimensional images; and manual input devices 1007, 1008,
by means of which a person (not shown), for example a
surgeon, may be able to telemanipulate robot arms 1002,
1003 in a first operating mode. Robotic surgical system 1000
may be configured for use on a patient 1013 lying on a
patient table 1012 to be treated in a minimally invasive
manner. Robotic surgical system 1000 may further include a
database 1014, in particular coupled to control device 1004,
in which are stored, for example, pre-operative data from
patient 1013 and/or anatomical atlases.

Each of the robot arms 1002, 1003 may include a plurality
of members, which are connected through joints, and an
attaching device 1009, 1011, to which may be attached, for
example, a surgical tool "ST" supporting an end effector
1050, 1060. One of the surgical tools "ST" may be surgical
instrument 100 (FIG. 1), surgical instrument 20 (FIG. 2), or
any other suitable surgical instrument 20 configured for use
in both an ultrasonic mode and one or more electrosurgical
(bipolar and/or monopolar) modes, wherein manual actua-
tion features, e.g., actuation button 120 (FIG. 1), clamp lever
130 (FIG. 1), etc., are replaced with robotic inputs. In such configurations, robotic surgical system 1000 may include or
be configured to connect to an ultrasonic generator, an
electrosurgical generator, and/or a power source. The other
surgical tool "ST" may include any other suitable surgical
instrument, e.g., an endoscopic camera, other surgical tool,
etc. Robot arms 1002, 1003 may be driven by electric drives,
e.g., motors, that are connected to control device 1004.
Control device 1004 (e.g., a computer) may be configured to
activate the motors, in particular by means of a computer
program, in such a way that robot arms 1002, 1003, their
attaching devices 1009, 1011, and, thus, the surgical tools
"ST" execute a desired movement and/or function according
to a corresponding input from manual input devices 1007,
1008, respectively. Control device 1004 may also be con-
figured in such a way that it regulates the movement of robot
arms 1002, 1003 and/or of the motors.

Figures 5, 6:
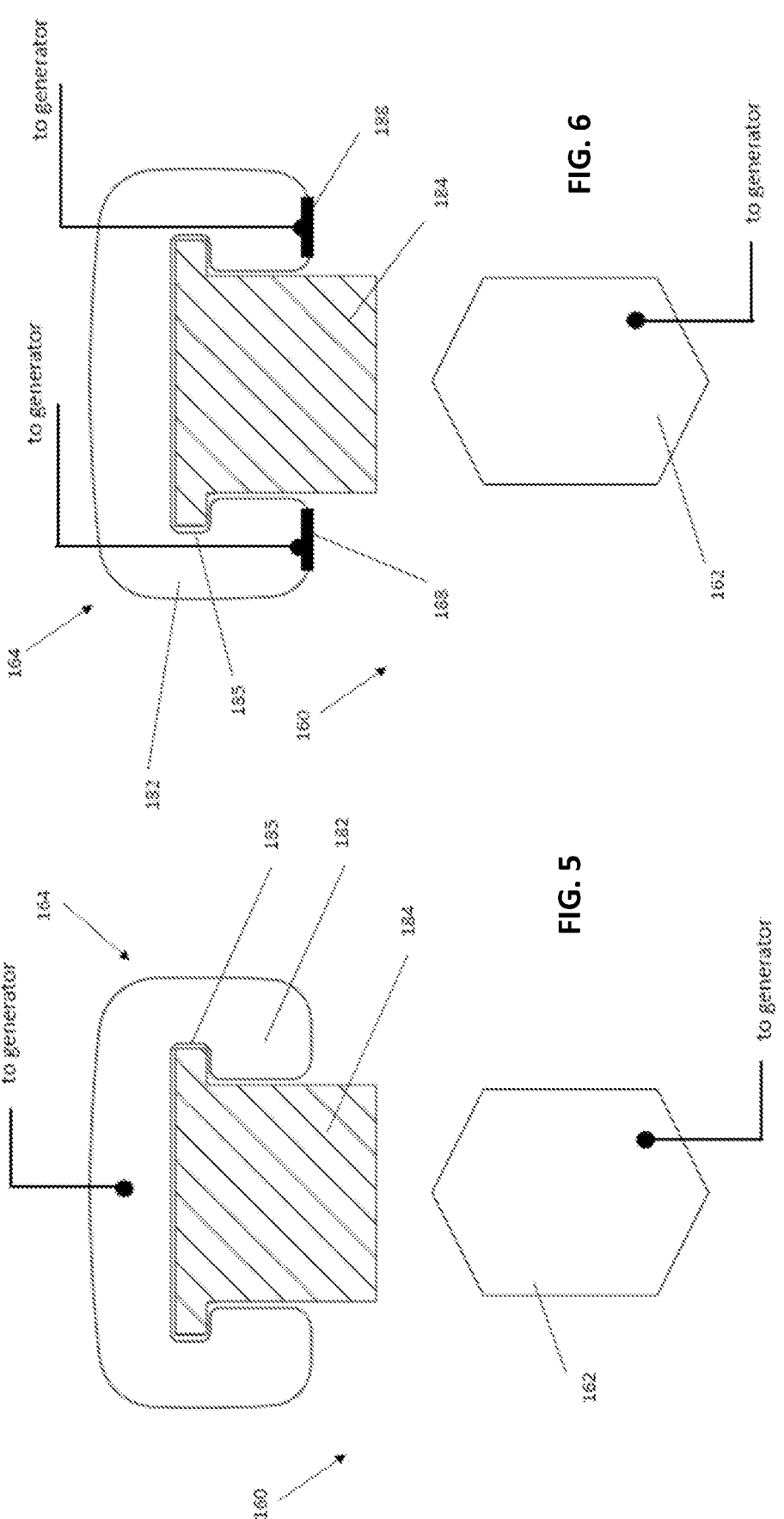
FIG. 5 is a transverse, cross-sectional view of the end effector assembly of the surgical instrument of FIG. 1.
FIG. 6 is a transverse, cross-sectional view of another configuration of the end effector assembly of the surgical instrument of FIG. 1.

Referring to FIGS. 4-6, end effector assembly 160 of
surgical instrument 100 of surgical system 10 (FIG. 1) is
detailed, although the aspects and features of end effector
assembly 160 may similarly apply, to the extent consistent,
to surgical instrument 20 (FIG. 2) and/or any other suitable
surgical instrument or system. End effector assembly 160, as
noted above, includes blade 162 and jaw member 164. Blade
162 may define a linear configuration, may define a curved
configuration, or may define any other suitable configura-
tion, e.g., straight and/or curved surfaces, portions, and/or
sections; one or more convex and/or concave surfaces,
portions, and/or sections; etc. With respect to curved con-
figurations, blade 162, more specifically, may be curved in
any direction relative to jaw member 164, for example, such
that the distal tip of blade 162 is curved towards jaw member
164, away from jaw member 164, or laterally (in either
direction) relative to jaw member 164. Further, blade 162
may be formed to include multiple curves in similar direc-
tions, multiple curves in different directions within a single
plane, and/or multiple curves in different directions in dif-
ferent planes. In addition, blade 162 may additionally or
alternatively be formed to include any suitable features, e.g.,
a tapered configuration, various different cross-sectional
configurations along its length, cut outs, indents, edges,
protrusions, straight surfaces, curved surfaces, angled sur-
faces, wide edges, narrow edges, and/or other features.

Blade 162 may define a polygonal, rounded polygonal, or
any other suitable cross-sectional configuration(s). Wave-
guide 154 or at least the portion of waveguide 154 proxi-
mally adjacent blade 162, may define a cylindrical shaped
configuration. Plural tapered surfaces (not shown) may
interconnect the cylindrically shaped waveguide 154 with
the polygonal (rounded edge polygonal, or other suitable
shape) configuration of blade 162 to define smooth transi-
tions between the body of waveguide 154 and blade 162.

Blade 162 may be wholly or selectively coated with a
suitable material, e.g., a non-stick material, an electrically
insulative material, an electrically conductive material, com-
binations thereof, etc. Suitable coatings and/or methods of
applying coatings include but are not limited to Teflon®,
polyphenylene oxide (PPO), deposited liquid ceramic insu-
lative coatings; thermally sprayed coatings, e.g., thermally
sprayed ceramic; Plasma Electrolytic Oxidation (PEO) coat-
ings; anodization coatings; sputtered coatings, e.g., silica;
ElectroBond® coating available from Surface Solutions
Group of Chicago, IL, USA; or other suitable coatings
and/or methods of applying coatings.

Continuing with reference to FIGS. 4-6, blade 162, as
noted above, in addition to receiving ultrasonic energy
transmitted along waveguide 154 from ultrasonic transducer
140 (FIG. 1), is adapted to connect to generator 200 (FIG.

1) to enable the supply of RF energy to blade 162 for conduction to tissue in contact therewith. In bipolar configurations, RF energy is conducted between blade 162 and jaw member 164 (or between portions of jaw member 164 and/or blade 162) and through tissue disposed therebetween to treat tissue. In monopolar configurations, RF energy is conducted from blade 162, serving as the active electrode, to tissue in contact therewith and is ultimately returned to generator 200 (FIG. 1) via return electrode device 500 (FIG. 1), serving as the passive or return electrode.

Jaw member 164 of end effector assembly 160 includes more rigid structural body 182 and more compliant jaw liner 184. Structural body 182 may be formed from an electrically conductive material, e.g., stainless steel, and/or may include electrically conductive portions. Structural body 182 includes a pair of proximal flanges 183a that are pivotably coupled to the inner support sleeve 153 via receipt of pivot bosses (not shown) of proximal flanges 183a within corresponding openings (not shown) defined within the inner support sleeve 153 and operably coupled with outer drive sleeve 152 via a drive pin 155 secured relative to outer drive sleeve 152 and pivotably received within apertures 183b defined within proximal flanges 183a. As such, sliding of outer drive sleeve 152 about inner support sleeve 153 pivots jaw member 164 relative to blade 162 from a spaced apart position to an approximated position to clamp tissue between jaw liner 184 of jaw member 164 and blade 162.

With reference to FIG. 5, structural body 182 may be adapted to connect to a source of electrosurgical energy, e.g., generator 200 (FIG. 1), and, in a bipolar electrosurgical mode, is charged to a different potential as compared to blade 162 to enable the conduction of bipolar electrosurgical (e.g., RF) energy through tissue clamped therebetween, to treat the tissue. In a monopolar electrosurgical mode, structural body 182 may be un-energized, may be charged to the same potential as compared to blade 162 (thus both defining the active electrode), or may be energized while blade 162 is not energized (wherein structural body 182 defines the active electrode). In either monopolar configuration, energy is returned to generator 200 (FIG. 1) via return electrode device 500 (FIG. 1), which serves as the passive or return electrode.

Referring to FIG. 6, as an alternative to the entirety of structural body 182 of jaw member 164 being connected to generator 200 (FIG. 1), the structural body may be formed from or embedded at least partially in an insulative material, e.g., an overmolded plastic. In such configurations, electrically conductive surfaces 188, e.g., in the form of plates, may be disposed on (e.g., bonded to, deposited onto, mechanically engaged with, etc.) or captured by the insulative material (e.g., overmolded plastic) to define electrodes on either side of jaw liner 184 on the blade facing side of jaw member 164. The electrically conductive surfaces 188, in such aspects, are connected to generator 200 (FIG. 1) and may be energized for use in bipolar and/or monopolar configurations, e.g., energized to the same potential as one another and/or blade 162 and/or different potentials as one another and/or blade 162. In aspects, electrically conductive surfaces 188 are disposed at additional or alternative locations on jaw member 164, e.g., along either or both sides thereof, along a back surface thereof, etc.

Again referring to FIGS. 4-6, jaw liner 184 is shaped complementary to a cavity 185 defined within structural body 182, e.g., defining a T-shaped configuration, to facilitate receipt and retention therein, although other configurations are also contemplated. Jaw liner 184 is fabricated from an electrically insulative, compliant material such as, for example, polytetrafluoroethylene (PTFE). The compliance of jaw liner 184 enables blade 162 to vibrate while in contact with jaw liner 184 without damaging components of ultrasonic surgical instrument 100 (FIG. 1) and without compromising the hold on tissue clamped between jaw member 164 and blade 162. Jaw liner 184 extends from structural body 182 towards blade 162 to inhibit contact between structural body 182 and blade 162 in the approximated position of jaw member 164. The insulation of jaw liner 184 maintains electrical isolation between blade 162 and structural body 182 of jaw member 164, thereby inhibiting shorting.

Figure 7:
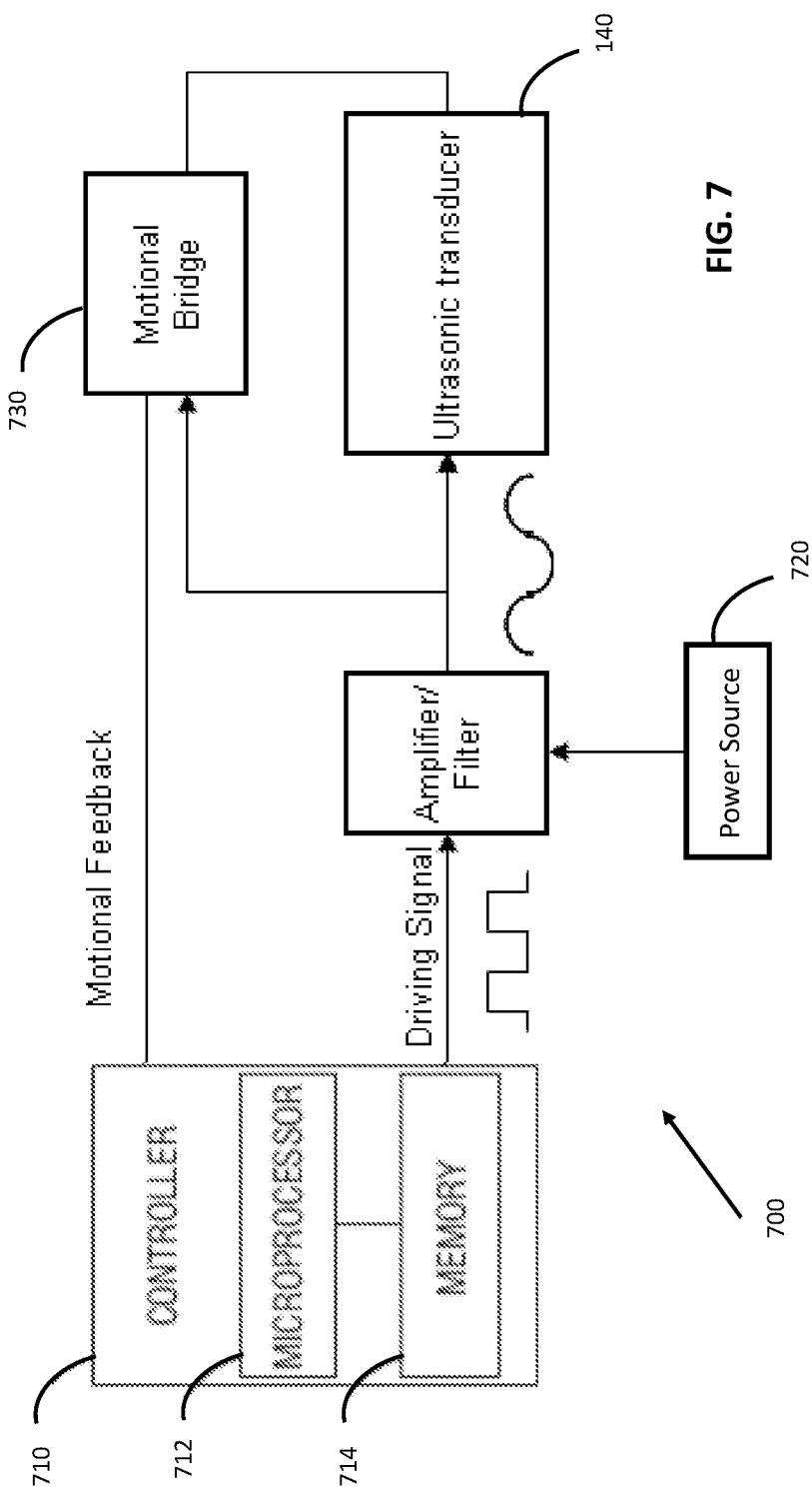
FIG. 7 is a simplified block diagram of an ultrasonic control system configured for use with the surgical systems of FIGS. 1-3 or any other suitable surgical system.

Turning to FIG. 7, an ultrasonic control system 700 of surgical instrument 100 of surgical system 10 (see FIG. 1) is detailed, although the aspects and features of ultrasonic control system 700 may similarly apply, to the extent consistent, to surgical instrument 20 (FIG. 2) and/or any other suitable surgical instrument or system. Ultrasonic control system 700 includes a controller 710 (e.g., of generator 200 (FIG. 1), ultrasonic generator 310 (FIG. 2), or any other suitable generator) and a power source 720 (e.g., generator 200 (FIG. 1), battery 400 (FIG. 2), or any other suitable power source) configured to control and power the electrical input to the ultrasonic transducer 140. Controller 710, more specifically, includes a microprocessor 712 and memory 714, e.g., storing instructions to be executed by microprocessor 712 to control the ultrasonic drive signal provided to ultrasonic transducer 140.

Ultrasonic control system 700 further includes a motional bridge 730 configured to sense a mechanical motion, e.g., a magnitude and frequency of mechanical motion, of ultrasonic transducer 140. The mechanical motion feedback provided by motional bridge 730 to controller 710 enables the controller 710 to control the frequency and/or magnitude of the driving signal, e.g., the high voltage AC driving signal, provided to ultrasonic transducer 140 to achieve a target amount of mechanical motion of ultrasonic transducer 140 at its resonance frequency. Controller 710 is also configured to monitor the resonant frequency of ultrasonic transducer 140, which varies throughout use such as, for example, due to changes in load applied to blade 162 (FIG. 4), temperature of blade 162 (FIG. 4), and/or other factors.

Figure 8:
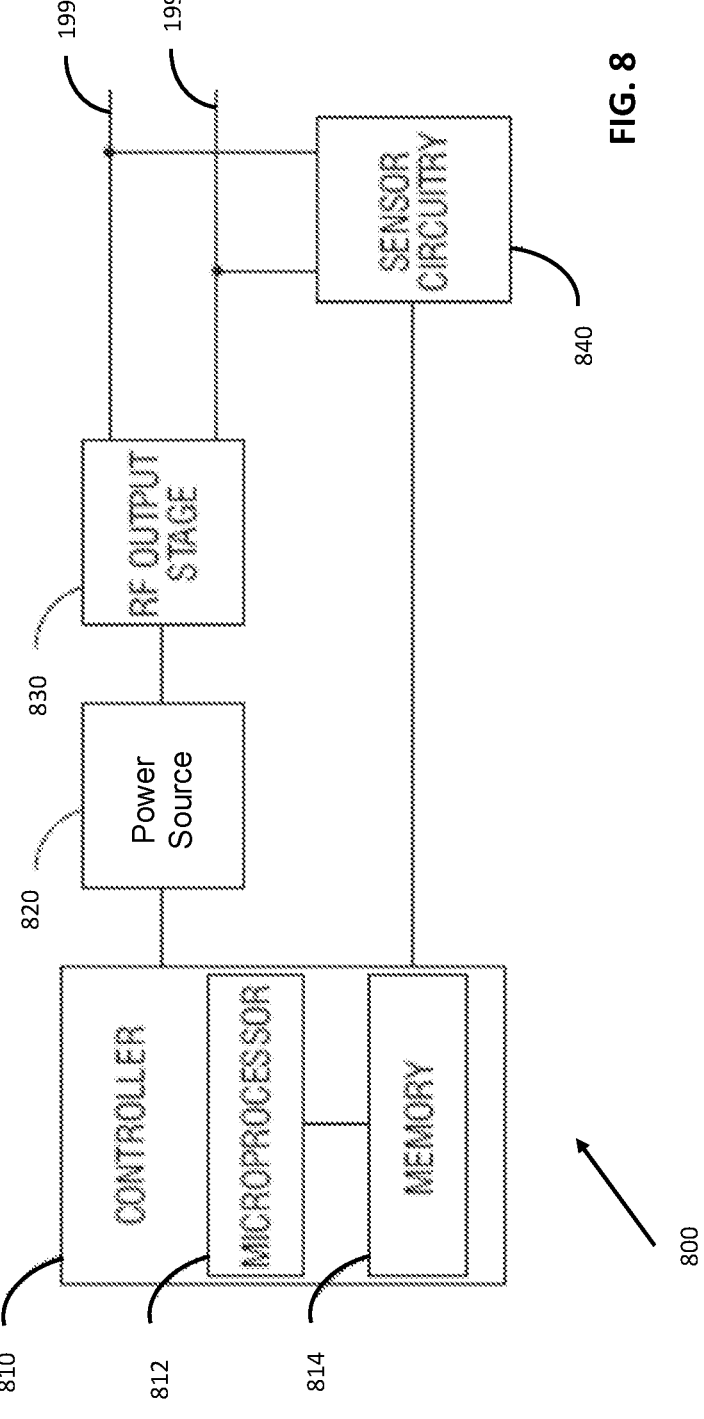
FIG. 8 is a simplified block diagram of an electrosurgical control system configured for use with the surgical systems of FIGS. 1-3 or any other suitable surgical system.

Referring to FIG. 8, an electrosurgical control system 800 of surgical instrument 100 of surgical system 10 (see FIG. 1) is detailed, although the aspects and features of electrosurgical control system 800 may similarly apply, to the extent consistent, to surgical instrument 20 (FIG. 2) and/or any other suitable surgical instrument or system. Electrosurgical control system 800 includes a controller 810 (e.g., of generator 200 (FIG. 1), electrosurgical generator 600 (FIG. 2), or any other suitable generator), a power source 820 (e.g., generator 200 (FIG. 1), battery 400 (FIG. 2), or any other suitable power source), an RF output stage 830, and sensor circuitry 840. Controller 810 includes a microprocessor 812 and memory 814, e.g., storing instructions to be executed by microprocessor 812 to control the electrosurgical energy output by RF output stage 830. Controller 810 (and/or microprocessor 812 and/or memory 814) may be the same controller 710 (and/or microprocessor 712 and/or memory 714) utilized in the ultrasonic control system 700 (FIG. 7) or may be a separate controller 810 (and/or microprocessor 812 and/or memory 814). Likewise, power source 820 may be the same power source 720 utilized in the ultrasonic control system 700 (FIG. 7) or may be a separate power source 820.

RF output stage 830, in a bipolar configuration(s), is configured to supply electrosurgical energy to jaw member 164, a portion of jaw member 164, and/or blade 162 of end effector assembly 160 (see FIG. 4) via one of electrical lead wires 199 and to return energy from jaw member 164, a portion of jaw member 164, and/or blade 162 of end effector assembly 160 (see FIG. 4) to complete the circuit back to electrosurgical control system 800 via the other electrical lead wire 199. In a monopolar configuration(s), RF output stage 830 supplies electrosurgical energy to jaw member 164, a portion of jaw member 164, and/or blade 162 of end effector assembly 160 (see FIG. 4) via one of electrical lead wires 199 to treat tissue while the energy is returned to complete the circuit back to electrosurgical control system 800 via return device 500 (FIG. 1).

Sensor circuitry 840 is operably coupled to wires 199 (or one wire 199 and return device 500 (FIG. 1)) so as to sense electrical parameters of the energy delivered to end effector assembly 160 (FIG. 4), e.g., voltage, current, resistance, etc. thereof, and, based thereon, determine one or more parameters of tissue, e.g., impedance of tissue, which can be utilized to determine whether tissue is sufficiently sealed (or a stage of tissue in the tissue sealing process), transected, or otherwise treated. Sensor circuitry 840 provides feedback, e.g., based on the sensed electrical parameter(s), to controller 810 and/or controller 710 of and/or ultrasonic control system 700 (FIG. 7), which, in turn, select an energy-delivery algorithm, modify an energy-delivery algorithm, and/or adjust energy-delivery parameters based thereon.

In addition or as an alternative to electrosurgical control system 800 controlling the supply of electrosurgical energy to treat tissue, electrosurgical control system 800 may also be configured to supply energy to tissue to interrogate tissue, e.g., wherein sensor circuitry 840 senses one or more electrical parameters to provide feedback to controller 810 such as, for example, to enable determination of the impedance of tissue. That is, instead of combined electrosurgical and ultrasonic tissue treatment, system 10 (FIG. 1), system 20 (FIG. 2), or any other suitable instrument or system in accordance with the present disclosure may be configured to treat tissue with ultrasonic energy while interrogating tissue with electrosurgical energy (without the need to supply tissue-treating electrosurgical energy as detailed above). Tissue interrogation may be initiated in a bipolar electrosurgical interrogation mode and/or a monopolar electrosurgical interrogation mode. In aspects, electrosurgical interrogating may be performed in the absence of any treatment energy, e.g., with the ultrasonic energy turned off, e.g., to assess tissue before treatment (e.g., to determine a type of treatment, a suitable energy delivery algorithm, and/or suitable energy delivery parameter), after treatment (e.g., to determine completion of tissue treatment and/or a state of treated or surrounding tissue), or in other circumstances.

With respect to interrogation of tissue, electrosurgical control system 800 is configured to transmit an interrogation signal according to any of the electrosurgical paths detailed above such that the signal is returned to electrosurgical control system 800 to enable evaluation thereof. The interrogation signal may be a continuous signal, a pulse signal, or a plurality of pulses. Electrosurgical control system 800, more specifically, is configured to evaluate the returned signal, e.g., the voltage, current, resistance, etc. thereof, and, based thereon, determine one or more parameters of tissue, e.g., the impedance of tissue, which is indicative of whether tissue is sufficiently sealed. Electrosurgical control system 800 and/or ultrasonic control system 700 (FIG. 7), in turn, select an energy-delivery algorithm, modify an energy-delivery algorithm, and/or adjust energy-delivery parameters based thereon.

Figure 9:
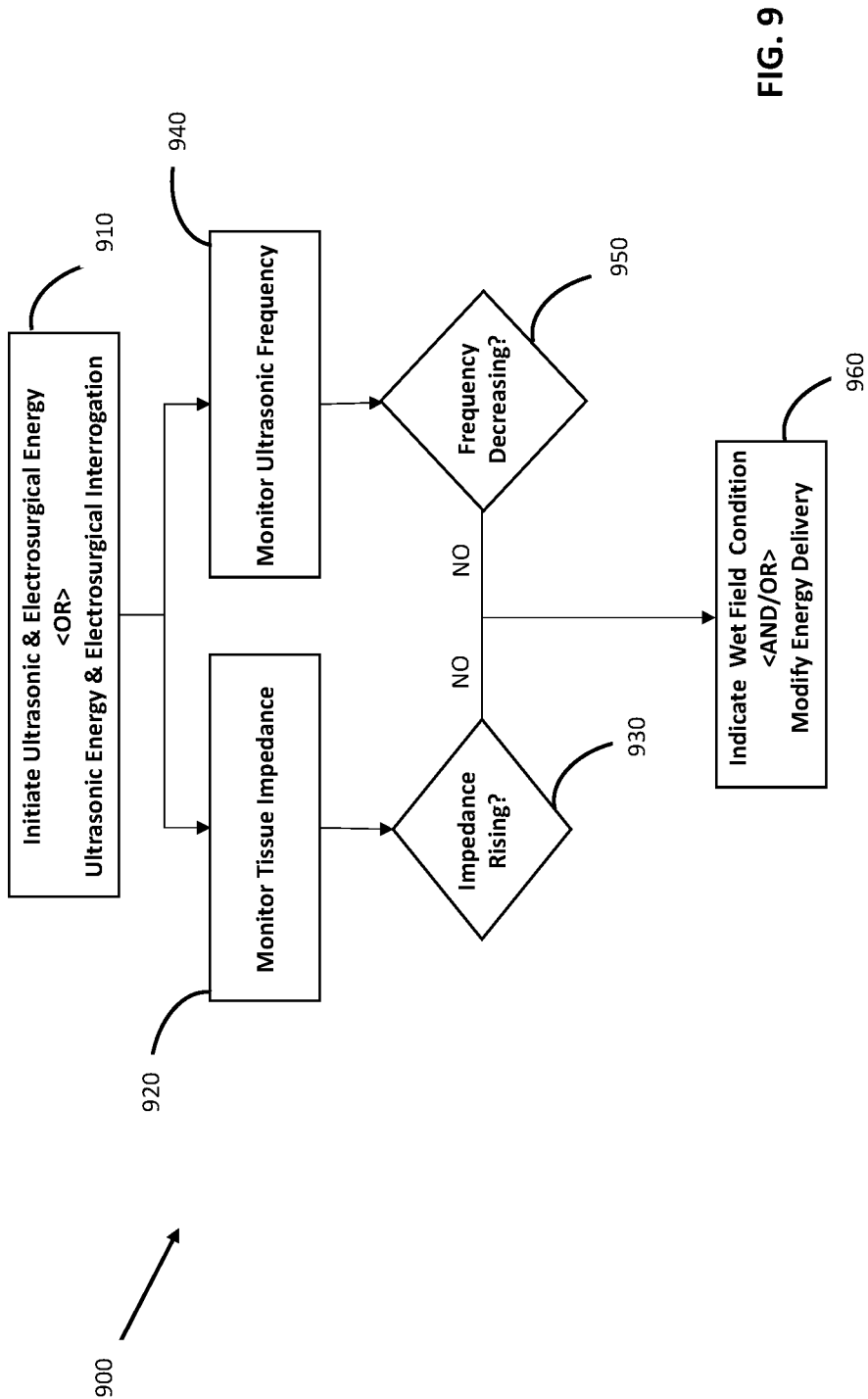
FIG. 9 is a flow diagram illustrating a method of wet field detection in accordance with the present disclosure.

Turning to FIG. 9, a method of detecting a wet field condition is shown generally as method 900. Method 900 may be implemented using surgical system 10 (FIG. 1) (e.g., ultrasonic control system 700 (FIG. 7) and electrosurgical control system 800 (FIG. 8) thereof), surgical instrument 20 (FIG. 2), and/or any other suitable surgical instrument or system. Treating tissue in a wet field may create complications in that electrosurgical energy may be conducted through the fluid in the field rather than through tissue clamped between the jaw member 164 and blade 162 (see FIG. 4), even after the clamped tissue is treated, e.g., after the tissue sealing cycle and/or tissue transection is complete. As such, impedance-based feedback indicative of properties of tissue, changes in tissue throughout tissue treatment, and/or completion of tissue treatment, e.g., completion of a tissue sealing cycle and/or tissue transection, may be limited or unavailable. As a result, the ability of electrosurgical control system 800 (FIG. 8) to determine energy-delivery parameters (based upon the properties of tissue) to be implemented, a tissue treatment algorithm to be implemented, and/or completion of tissue treatment (or stages thereof, where a multi-stage algorithm is utilized) may be compromised. Method 900, as detailed below, enables detection of a wet field condition to enable, in response to detecting a wet field condition, output of indication to alert the user as to the wet field condition and/or to automatic modification of the energy delivered. However, although method 900 is detailed with respect to determining a wet field condition, the present disclosure also contemplates that method 900 may likewise apply to determining any other suitable field and/or tissue condition based on both electrosurgical and ultrasonic feedback and, in response to determining that the field and/or tissue condition exists, providing an indication of the same and/or modifying energy delivery accordingly.

Method 900 begins at 910, wherein ultrasonic and electrosurgical treatment energy are initiated or wherein ultrasonic treatment energy is initiated with electrosurgical interrogation energy. Ultrasonic energy and electrosurgical energy (whether treatment energy or interrogation energy) may be initiated simultaneously, overlapping, alternatively, or in any other suitable manner. For example, and with momentary reference to FIGS. 5 and 6, with tissue clamped between blade 162 and jaw liner 184 of jaw member 164, ultrasonic energy produced by ultrasonic transducer 140 (FIG. 1) may be transmitted along waveguide 154 to blade 162 to facilitate treating tissue clamped between blade 162 and jaw liner 184 of jaw member 164, and body 182 of jaw member 164 and blade 162 may be charged with electrosurgical energy at different potentials to enable the conduction of bipolar electrosurgical (e.g., RF) energy therebetween and through the clamped tissue to facilitate treating the clamped tissue and/or to enable interrogation of the clamped tissue.

With respect to sealing tissue (using both ultrasonic and electrosurgical treatment energy or ultrasonic energy with electrosurgical interrogation), for example, electrosurgical control system 800 (FIG. 8) is capable of monitoring impedance of tissue to control power and/or other parameters (of RF energy and/or ultrasonic energy) and/or to determine the completion of tissue sealing. The RF impedance of tissue in a dry field is expected to decrease initially as the tissue warms up, then increase as the tissue is desiccated (desiccation may thus be indicated by a rise in impedance within a defined time limit associated with the sealing algorithm implemented and/or parameters thereof). If the above impedance pattern (e.g., an impedance drop followed by a rise) or a portion thereof (such as the rise in impedance indicating desiccation) is not detected within defined time limit(s), a timeout error may be triggered, indicating a potential error in the sealing process and, thus, an incomplete and/or inadequate tissue seal. However, as noted above, if the tissue being sealed is within a wet field, the impedance feedback may not be indicative of the impedance of the clamped tissue to be sealed but may be at least partially from the fluid in the field through which the electrosurgical energy is conducted and, thus, the impedance feedback may be unreliable.

Accordingly, as indicated at 920 of method 900 of FIG. 9, tissue impedance is monitored. Impedance may be monitored, for example, for a rise, other change, and/or other temporal pattern of impedance indicative of completion of a tissue seal, as indicated at 930. Determining whether there is a rise in impedance, other change in impedance, or whether the impedance follows an expected pattern may include monitoring impedance relative to a particular threshold impedance value, monitoring impedance over time relative to a particular threshold impedance ramp (e.g., impedance change over time), and/or monitoring a change in impedance relative to a threshold impedance change. Impedance may be monitored to determine a rise, other change, and/or pattern in impedance within a defined timeframe, after a defined time, and/or in any other suitable manner. As an alternative or in addition to monitoring for a rise, other change, and/or pattern in impedance indicative of completion of a tissue seal, other changes in impedance and/or other electrical parameters may be monitored relative to a particular threshold value, ramp, change, etc., and/or impedance and/or other electrical parameters may be monitored for another purpose, e.g., indicating a state of tissue, indicating completion of a stage of tissue sealing, indicating completion of tissue transection, etc. For the purposes of providing an example, impedance is monitored hereinbelow for detecting a rise in impedance although, as noted above, other configurations are also contemplated. Further, it is noted that any of the threshold values noted herein are not necessarily pre-determined values but may be dynamically calculated valves based on feedback. Likewise, the threshold values noted herein need not be absolute valves but may be relative values (e.g., percentages of or multipliers of sensed or other threshold values).

During the supply of ultrasonic energy, e.g., for tissue sealing or other tissue treatment, as noted above, ultrasonic control system 700 (FIG. 7) monitors the resonant frequency of ultrasonic transducer 140 (FIG. 7) and controls the frequency and/or magnitude of the driving signal provided to ultrasonic transducer 140 (FIG. 7) to achieve a target amount of mechanical motion of ultrasonic transducer 140 (FIG. 7) at its resonance frequency. Monitoring the resonant frequency of ultrasonic transducer 140 (FIG. 7), indicated at 940, provides information relating to the ultrasonic system. For example, the resonant frequency varies based on certain factors such as temperature of blade 162 (FIG. 4); thus, monitoring the ultrasonic resonant frequency at 940 may be utilized as a proxy for monitoring temperature of blade 162 (FIG. 4).

More specifically, with tissue clamped between blade 162 and jaw liner 184 of jaw member 164 (see FIG. 5) and ultrasonic vibration energy being transmitted from blade 162 (FIG. 5) to the clamped tissue, tissue is heated to facilitate treatment thereof and blade 162 (FIG. 5) is also heated. This heating of blade 162 (FIG. 5) during use results in a corresponding decrease in resonant frequency. However, if the tissue being treated is within a wet field, the fluid surrounding blade 162 (FIG. 5) may absorb heat from blade 162 (FIG. 5) thus cooling (e.g., reducing heating of or slowing heating of) blade 162 and, as a result, reducing, slowing, or eliminating the decrease in resonant frequency normally associated with use of ultrasonic energy to treat tissue. Thus, if a lack of decrease in resonant frequency is detected, a potential wet field condition may exist.

As indicated at 950 of method 900 of FIG. 9, the ultrasonic resonant frequency may be monitored to determine whether the ultrasonic resonant frequency is decreasing and, thus whether blade temperature is rising. Determining whether the ultrasonic resonant frequency is decreasing may include monitoring the frequency relative to a particular threshold frequency value, monitoring frequency over time relative to a particular threshold frequency ramp, and/or monitoring a change in frequency relative to a threshold frequency change. Frequency may be monitored to determine a decrease in frequency within a defined timeframe, after a defined time, and/or in any other suitable manner. As an alternative or in addition to frequency for a decrease in frequency indicative of a rise in blade temperature, other changes in frequency and/or other mechanical motion parameters may be monitored relative to a particular threshold value, ramp, change, etc., and/or frequency and/or other mechanical motion parameters may be monitored for another purpose, e.g., indicating a state of tissue, indicating completion of a stage of tissue sealing, indicating completion of tissue transection, indicating contact with a metal object or bone, etc.

If it is determined at 930 that impedance is not rising ("NO" at 930) and at 950 that frequency is not decreasing ("NO" at 950), it can be determined that a wet field condition exists since, as detailed above, both the lack of an expected impedance rise and the lack of an expected frequency decrease are indicative of a potential wet field condition separately; together, the lack of an expected impedance rise and the lack of an expected frequency decrease provide a strong indication that there is indeed a wet field condition. At 960, in response to determining that a wet field condition exists, an indication, e.g., an audio alert, haptic feedback, a visual alert (flashing LED), visual display (on an GUI associated with the surgical system (e.g., the generator thereof) and/or on other operating room device(s)), etc. is provided to indicate to the user that a wet field condition exits, e.g., to enable the user to check conditions, modify a treatment course and/or energy delivery, clear the wet field, etc. Additionally or alternatively, energy delivery is modified automatically at 960. With respect to modification of energy delivery in response to determining that a wet field condition exists, all energy delivery may be turned OFF, all energy delivery may be paused for a defined time, electrosurgical energy may be turned OFF while ultrasonic energy continues (or vice versa), an alternate tissue treatment algorithm may be implemented (e.g., for tissue sealing: rather than an impedance-based algorithm, a time and/or power-based algorithm may be implemented), combinations thereof, etc.

In the event an impedance rise is not detected but a frequency decrease is detected, an error may be triggered, e.g., a timeout error by the generator, an indication may be provided, and/or energy delivery may be modified, depending upon a particular situation. In some situations, rather than an error being triggered, the impedance and frequency may continue to be monitored for at least a period of time, to enable further determination of the condition. For example, a frequency decrease coupled with a lack of impedance rise may be the result of a wet field or partial wet-field condition where the blade is heating up, e.g., at start-up, and where there is not (yet) enough fluid between the blade and jaw member to cause a short. By continuing to monitor the impedance and frequency, a subsequent determination of whether there is a wet field (or error) can be made. Likewise, in the event an impedance rise is detected but a frequency decrease is not detected, an error may be triggered, an indication may be provided, energy delivery may be modified, and/or monitoring may continue for a period of time.

While several aspects of the disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular aspects. Those skilled in the art will envision other modifications within the scope and spirit of the claims appended hereto.

What is claimed is:

1. A surgical system, comprising:
an ultrasonic blade operably coupled to an ultrasonic transducer for receiving ultrasonic energy produced by the ultrasonic transducer;
a jaw member pivotable relative to the ultrasonic blade between a spaced-apart position and an approximated position for clamping tissue between the ultrasonic blade and the jaw member, wherein a portion of the jaw member is adapted to connect to a source of electro-surgical energy at a first potential and another portion of the jaw member or the ultrasonic blade is adapted to connect to the source of electrosurgical energy at a second potential different from the first potential to conduct electrosurgical energy therebetween and through the clamped tissue, and wherein the ultrasonic blade is configured to transmit ultrasonic energy to the tissue clamped between the ultrasonic blade and the jaw member; and
at least one controller configured to monitor a resonant frequency associated with the ultrasonic energy and to monitor an impedance of the clamped tissue associated with the electrosurgical energy and to determine whether an adverse condition exists based on the monitoring of the resonant frequency and the monitoring of the impedance of the clamped tissue, wherein the controller is configured to determine that an adverse condition exists when it is determined that an expected change in impedance did not occur and that an expected decrease in resonant frequency did not occur.

2. The surgical system according to claim 1, wherein the controller is further configured, in response to determining that the adverse condition exists, to provide an indication that the adverse condition exists.

3. The surgical system according to claim 1, wherein the controller is further configured, in response to determining that the adverse condition exists, to modify at least one of the ultrasonic energy or the electrosurgical energy.

4. The surgical system according to claim 1, wherein the controller is further configured, in response to determining that the adverse condition exists, to turn off at least one of the ultrasonic energy or the electrosurgical energy.

5. The surgical system according to claim 1, wherein the electrosurgical energy is configured to facilitate tissue treatment in conjunction with the ultrasonic energy.

6. The surgical system according to claim 1, wherein the ultrasonic energy is configured to treat tissue and the electrosurgical energy is configured to interrogate tissue.

7. The surgical system according to claim 1, wherein monitoring the resonant frequency includes monitoring at least one of: a value of the resonant frequency, a ramp of the resonant frequency, or a change in the resonant frequency.

8. The surgical system according to claim 1, wherein monitoring the impedance of the clamped tissue includes monitoring at least one of: a value of the impedance, a ramp of the impedance, or a change in the impedance.

9. A method of energy-based tissue treatment, comprising:
transmitting ultrasonic energy, via an ultrasonic blade, to tissue clamped between the ultrasonic blade and a jaw member;
energizing a portion of the jaw member with electrosurgical energy at a first potential and energizing another portion of the jaw member or the ultrasonic blade with electrosurgical energy at a second potential different from the first potential to conduct electrosurgical energy therebetween and through the clamped tissue;
monitoring a resonant frequency associated with the ultrasonic energy;
monitoring an impedance of the clamped tissue associated with the electrosurgical energy; and
determining whether an adverse condition exists based on the monitoring of the resonant frequency and the monitoring of the impedance, wherein it is determined that an adverse condition exists when it is determined that an expected change in impedance did not occur and that an expected decrease in resonant frequency did not occur.

10. The method according to claim 9, further comprising, in response to determining that the adverse condition exists, providing an indication that the adverse condition exists.

11. The method according to claim 9, further comprising, in response to determining that the adverse condition exists, modifying at least one of the ultrasonic energy or the electrosurgical energy.

12. The method according to claim 9, further comprising, in response to determining that the adverse condition exists, turning off at least one of the ultrasonic energy or the electrosurgical energy.

13. The method according to claim 9, wherein the electrosurgical energy is configured to facilitate tissue treatment in conjunction with the ultrasonic energy.

14. The method according to claim 9, wherein the ultrasonic energy is configured to treat tissue and the electrosurgical energy is configured to interrogate tissue.

15. The method according to claim 9, wherein the monitoring of the resonant frequency includes monitoring at least one of: a value of the resonant frequency, a ramp of the resonant frequency, or a change in the resonant frequency.

16. The method according to claim 9, wherein the monitoring of the impedance includes monitoring at least one of: a value of the impedance, a ramp of the impedance, or a change in the impedance.

17. A surgical system, comprising:
an ultrasonic blade operably coupled to an ultrasonic transducer for receiving ultrasonic energy produced by the ultrasonic transducer;
a jaw member pivotable relative to the ultrasonic blade between a spaced-apart position and an approximated position for clamping tissue between the ultrasonic blade and the jaw member, wherein a portion of the jaw member is adapted to connect to a source of electro-surgical energy at a first potential and another portion of the jaw member or the ultrasonic blade is adapted to connect to the source of electrosurgical energy at a second potential different from the first potential to conduct electrosurgical energy therebetween and through the clamped tissue, and wherein the ultrasonic blade is configured to transmit ultrasonic energy to the tissue clamped between the ultrasonic blade and the jaw member; and at least one controller configured to monitor a resonant frequency associated with the ultrasonic energy and to monitor an impedance of the clamped tissue associated with the electrosurgical energy and to determine whether an adverse condition exists based on the monitoring of the resonant frequency and the monitoring of the impedance of the clamped tissue, wherein the controller is configured to determine that a wet field condition exists when it is determined that an expected change in impedance did not occur and that an expected decrease in resonant frequency did not occur.

18. The surgical system according to claim 17, wherein the expected change in impedance is an expected increase in impedance.

19. The surgical system according to claim 17, wherein the controller is further configured, in response to determining that the wet field condition exists, to turn off at least one of the ultrasonic energy or the electrosurgical energy.

20. The surgical system according to claim 17, wherein monitoring the impedance of the clamped tissue includes monitoring at least one of: a value of the impedance, a ramp of the impedance, or a change in the impedance.

\* \* \* \* \*